(12) United States Patent
Kanazawa et al.

(10) Patent No.: US 7,632,656 B2
(45) Date of Patent: Dec. 15, 2009

(54) HIGH PERFORMANCE LIQUID CHROMATOGRAPHY WITH AN AQUEOUS MOBILE PHASE FOR ANALYSIS OF DRUG AND ITS METABOLITE

(75) Inventors: Hideko Kanazawa, Sagamihara (JP); Teruo Okano, Ichikawa (JP)

(73) Assignees: Cellseed Inc., Tokyo (JP); Hideko Kanazawa, Kanagawa (JP)

( * ) Notice: Subject to any disclaimer, the term of this patent is extended or adjusted under 35 U.S.C. 154(b) by 124 days.

(21) Appl. No.: 10/547,751

(22) PCT Filed: Mar. 4, 2004

(86) PCT No.: PCT/JP2004/002753

§ 371 (c)(1),
(2), (4) Date: Jun. 7, 2006

(87) PCT Pub. No.: WO2004/078968

PCT Pub. Date: Sep. 16, 2004

(65) Prior Publication Data

US 2006/0228770 A1    Oct. 12, 2006

(30) Foreign Application Priority Data

Mar. 4, 2003 (JP) ............................ 2003-104625

(51) Int. Cl.
*C12Q 1/26* (2006.01)
(52) U.S. Cl. .......................................... 435/25
(58) Field of Classification Search .................... 435/25
See application file for complete search history.

(56) References Cited

U.S. PATENT DOCUMENTS

| | | | |
|---|---|---|---|
| 5,929,214 A | 7/1999 | Peters | |
| 6,706,187 B1 | 3/2004 | Okano et al. | |

FOREIGN PATENT DOCUMENTS

| | | |
|---|---|---|
| EP | 1 081 492 A1 | 3/2001 |
| JP | 2002-020318 | 1/2002 |
| WO | 01/09198 | 2/2001 |
| WO | WO 02/04660 A2 * | 1/2002 |
| WO | 02/52044 | 7/2002 |

OTHER PUBLICATIONS

Dierks, E. et al. A Method for the Simultaneous Evaluation of the Activities of Seven Major Human Drug Metabolizing Cytochrome P450S . . . Drug Metabolism Disposition 29(1)23-29 2001.*
Kanazawa H. et al. Analysis of Peptides and Proteins by Temperature Responsive Chromatographic System . . . J of Pharmaceutical and Biomedical Analysis 15(9-10)1545-1550, Jun. 1997.*
Kanazawa H. et al. Temperature Responsive Liquid Chromatography. Analysis Chemistry 69(5)823-830, Mar. 1 1997.*
Kanazawa H. et al. Temperature Responsive Chromatography Using Poly(N-Isopropylacrylamide) Hydrogel Modified Siliica. Analytical Sciences 18(1)45-48, Jan. 2002.*
Kanazawa H. et al. Temperature Responsive Chromatography. Trends in Analytical Chemistry 17(7)435-440, 1998.*
Lange et al., *Interaction of tryptophan residues of cytochrome P450scc with a highly specific fluorescence quencher, a substrate analogue, compared to acrylamide and iodide*, European Journal of Biochemistry, vol. 226, No. 3, 1994, pp. 963-970.
Kanazawa et al, "Temperature-Responsive Liquid Chromatography 2. Effects of Hydrophobic Groups in N-Isopropylacrylamide Copolymer-Modified Silica", Analytical Chemistry, American Chemical Society, Columbus, U.S., vol. 69, No. 5, Mar. 1, 1997, pp. 823-830, XP002922237.
Malmstadt et al, "A smart microfluidic affinity chromatography matrix composed of poly(N-isopropylacrylamide)-coated beads", Analytical Chemistry Jul. 1, 2003 U.S., vol. 75, No. 13, pp. 2943-2949, XP002429860.
Ivanov et al, "Effect of temperature upon the chromatography of proteins on porous glass, chemically coated with N-isopropylacrylamide copolymer", Journal of Chromatography A, Elsevier, Amsterdam, NL, vol. 776, No. 1, Jul. 25, 1997, pp. 78-80, XP004125540.

* cited by examiner

*Primary Examiner*—Ralph Gitomer
(74) *Attorney, Agent, or Firm*—Nixon & Vanderhye P.C.

(57) ABSTRACT

The amount of drug consumption caused by a specific drug-metabolizing enzyme and/or the amount of the resulting metabolite(s) is measured by chromatography with an aqueous mobile phase under temperature control using a packing material whose surface is coated with a polymer having a hydration force varying in the temperature range of 0° C. to 80° C. This system enables proper evaluation of drug-metabolizing capacity through simple means without adversely affecting the environment.

15 Claims, 5 Drawing Sheets a) Measurement temperature: 10°C b) Measurement temperature: 40°C

Simultaneous analysis of probe drugs

1: S-Mephenytoin
2: Phenacetin
3: Coumarin
4: Chlorzoxazone
5: Tolbutamide
6: Testosterone

HIGH PERFORMANCE LIQUID CHROMATOGRAPHY WITH AN AQUEOUS MOBILE PHASE FOR ANALYSIS OF DRUG AND ITS METABOLITE

This application is the US national phase of international application PCT/JP2004/002753 filed 4 Mar. 2004 which designated the U.S. and claims benefit of JP 2003-104625, filed 4 Mar. 2003, the entire contents of each of which are hereby incorporated by reference.

TECHNICAL FIELD

The present invention relates to a novel evaluation system for drug-metabolizing capacity, in which a packing material whose surface is coated with a polymer having a hydration force varying in the temperature range of 0° C. to 80° C. is used for chromatography with an aqueous mobile phase to measure under temperature control the function of drug metabolism in the fields of biology, medicine, pharmacy, etc.

BACKGROUND ART

In order to analyze drug interactions in humans and human gene polymorphisms, recent attention has been focused on in vivo drug metabolism. Also in the development of new drugs, the importance of studying in vivo drug metabolism is widely recognized and efforts are made to elucidate phenomena related to the effectiveness or toxicity of drugs by monitoring qualitative and quantitative changes in the drugs administered in vivo.

Although drug metabolism occurs in many tissues in the body, the major metabolic site for most drugs is the liver in terms of its high activity and weight. In the metabolism of fat-soluble drugs, a particularly important role is played by cytochrome P450 (forming a superfamily, abbreviated as CYP) which is localized in microsomes and categorized as a so-called drug-metabolizing enzyme. The basic reaction mechanism of this enzyme involves drug oxidation reaction resulting from oxygen activation mediated by cytochrome P450 reduced by the action of NADPH-cytochrome P450 reductase, as well as drug reduction reaction due to a low oxidation-reduction potential of cytochrome P450. It is currently reported that 80% or more of the clinically used drugs are metabolized by P450. In particular, metabolites produced as a result of oxidation reaction (Phase I reaction) are further metabolized into more water-soluble metabolites through glucuronide conjugation, sulfate conjugation, amino acid conjugation, acetyl conjugation, glutathione conjugation or the like (Phase II), thereby facilitating their excretion into urine or bile.

This P450 metabolism study has been conventionally conducted using reversed-phase chromatography in which a hydrophobic porous silica gel whose surface is modified with octadecyl groups is used as a stationary phase and solutes are separated by continuously increasing the concentration of an organic solvent in a mobile phase. However, organic solvents and buffers used in conventional mobile phases provide eluates containing contaminants and are disadvantageous in that baseline stabilization and detection sensitivity are significantly decreased because the contaminants produce strong UV absorption. Moreover, a column is required to be washed and equilibrated with an initial eluent before being continuously provided for the next analysis, which constitutes an additional disadvantage of prolonged analysis time. Further, detailed separation conditions including the flow rate, ionic strength and pH of eluent as well as column temperature should be determined for each solute; for example, in a clinical setting or elsewhere, there has been a strong demand for a simple method which allows separation of individual solutes under a single condition.

In the current clinical setting, an antigen-antibody reaction-based immunoassay (TDX) is actually used as a method for simple evaluation of drug-metabolizing capacity. However, such a method permits the measurement of only one item and hence requires repeated measurements when a larger number of items should be measured. Under present circumstances, such a method is therefore cost consuming and involves complicated steps.

DISCLOSURE OF THE INVENTION

The present invention is intended to solve the above problems of conventional techniques. Namely, an object of the present invention is to provide an evaluation system for drug-metabolizing capacity which is conveniently available even in a clinical setting. Another object of the present invention is to provide the use of this evaluation system.

To solve the above problems, the inventors of the present invention have made investigations from various angles to conduct research and development. As a result, the inventors have found that a simple evaluation system for drug-metabolizing capacity can be obtained when the amount of drug consumption caused by a specific drug-metabolizing enzyme and/or the amount of the resulting metabolite(s) is measured by chromatography with an aqueous mobile phase under temperature control using a packing material whose surface is coated with a polymer having a hydration force varying in the temperature range of 0° C. to 80° C. This finding led to the completion of the present invention.

Namely, the present invention provides an evaluation system for drug-metabolizing capacity which is conveniently available even in a clinical setting.

Also, the present invention provides an evaluation method for drug-metabolizing capacity, which uses the evaluation system for drug-metabolizing capacity.

In addition, the present invention provides an evaluation method for cytochrome P450 genetic polymorphism, which uses the evaluation system for drug-metabolizing capacity.

Moreover, the present invention provides a diagnostic method for cirrhosis and/or liver cancer, which uses the evaluation system for drug-metabolizing capacity.

BEST MODE FOR CARRYING OUT THE INVENTION

Figure 1:
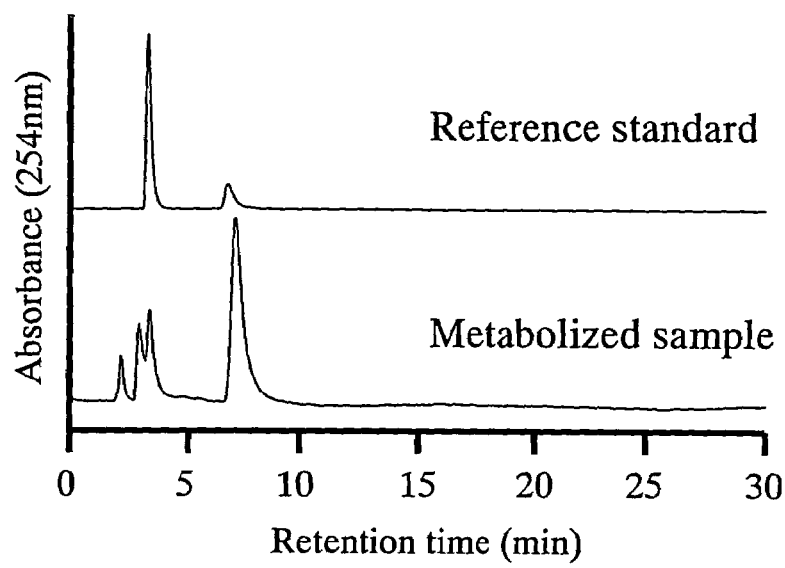
FIG. 1 presents charts showing the absorbance of testosterone and its metabolite measured at 254 nm under temperature conditions of 10° C. and 40° C.
Figure 1:
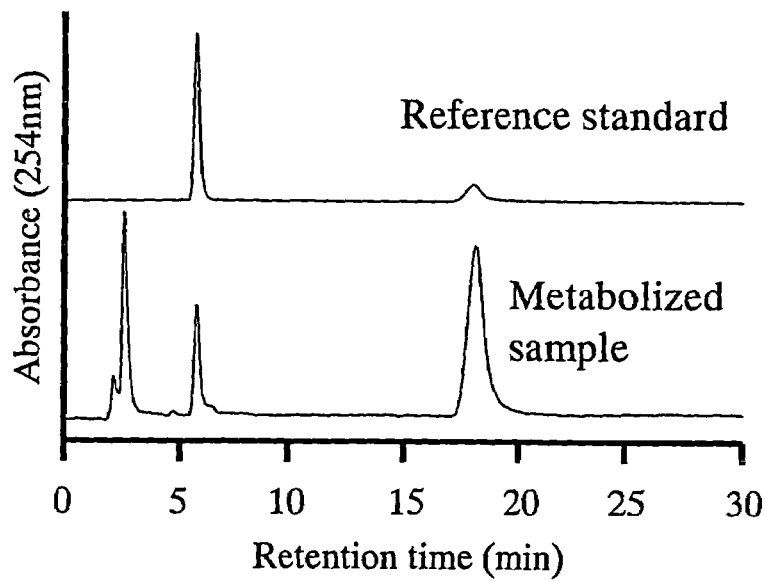

In the present invention, it has been found that an evaluation system for drug-metabolizing capacity which allows not only simple measurement, but also simultaneous measurement of the amount of drug consumption caused by a plurality of drug-metabolizing enzymes and/or the amount of the resulting metabolite(s) can be obtained when the amount of drug consumption caused by a specific drug-metabolizing enzyme and/or the amount of the resulting metabolite(s) is measured by chromatography with an aqueous mobile phase under temperature control using a packing material whose surface is coated with a polymer having a hydration force varying in the temperature range of 0° C. to 80° C.

Representative examples of drug-metabolizing enzymes used in the present invention include cytochrome P450 molecular species, alcohol dehydrogenase, esterase, β-glucuronidase, flavin-containing monooxygenase, aldehyde dehydrogenase, monoamine oxidase, NAD(P)H-quinone reductase, NADPH—P450 reductase, aldehyde reductase, ketone reductase, epoxy hydrolase, sulfatase, cysteinylglycinase, γ-glutamate transferase, UDP-glucuronide transferase, sulfate transferase, glutathione S-transferase, N-acetyltransferase, glycine-conjugating enzyme, methylation enzyme, glucose transferase and rhodanese. These enzymes may be used either alone or in combination, and their type is not limited in any way.

Examples of cytochrome P450 molecular species in the present invention include, for example, CYP1A1, CYP1A2, CYP2A6, CYP2B6, CYP2C8, CYP2C9, CYP2C19, CYP2D6, CYP2E1, CYP2F1, CYP3A3, CYP3A4, CYP3A7, CYP2A1, CYP2A2, CYP2A4, CYP2A5, CYP2B1, CYP2B2, CYP2B4, CYP2B5, CYP2B9, CYP2C2, CYP2C3, CYP2C4, CYP2C5, CYP2C6, CYP2C7, CYP2C11, CYP2C12, CYP2C14, CYP2C29, CYP2D1, CYP2D2, CYP2D9, CYP2F2, CYP2G1, CYP3A1, CYP3A2, CYP3A6, CYP4A1 and CYP4B1. These members may be used either alone or in combination, and their type is not limited in any way.

In the present invention, a polymer coated over the surface of a packing material causes hydration/dehydration according to the changes of temperature, which in turn alters the hydrophilic/hydrophobic balance on the packing material surface. To achieve this, for example, a polymer responsive to the changes of temperature may be introduced into the surface of the packing material.

The polymer coated over the packing material of the present invention causes hydration/dehydration according to the changes of temperature. The required temperature range was found to be 0° C. to 80° C., preferably 10° C. to 50° C., and more preferably 20° C. to 45° C. Temperatures exceeding 80° C. are not preferable because the handling will be affected, e.g., by evaporation of water used as a mobile phase. Likewise, temperatures lower than 0° C. are also not preferable because the mobile phase may be frozen.

The above polymer responsive to the changes of temperature (hereinafter referred to as the "temperature-responsive polymer") used in the present invention may be either a homopolymer or a copolymer. Examples of such a polymer include, for example, those described in JP 2-211865 A. More specifically, such a polymer may be obtained, e.g., by homopolymerization or copolymerization of the following monomers. Monomers available for use include, for example, (meta)acrylamide compounds ((meta)acrylamide is intended to mean both acrylamide and methacrylamide, the same applying hereinafter), N-(or N,N-di)alkyl-substituted (meta) acrylamide derivatives, or vinyl ether derivatives. In the case of copolymers, any two or more of these monomers may be used. Moreover, it is also possible to use copolymerization with any monomers other than those listed above, graft polymerization or copolymerization between polymers, or mixtures of polymers or copolymers. Likewise, it is also possible to effect crosslinking as long as the properties inherent to polymers are not impaired.

In the present invention, the mobile phase is kept as aqueous. As used herein, the term "aqueous" is intended to mean water alone or an aqueous solution that contains an inorganic salt(s), but is free from any organic solvent. In this case, "water" refers to any one of distilled water, deionized water or purified water.

According to the present invention, the amount of drug consumption caused by a specific drug-metabolizing enzyme and/or the amount of the resulting metabolite(s) is measured by chromatography with an aqueous mobile phase under temperature control. Samples used for the measurement include, without any limitation, those containing a mixture of a specific drug-metabolizing enzyme and a drug and/or its metabolite(s), as well as those pre-treated to remove a specific drug-metabolizing enzyme. In particular, the present invention uses an aqueous mobile phase and hence has no risk of solvent-induced denaturation of a specific drug-metabolizing enzyme. The present invention therefore enables direct measurement of the former sample in the form of a mixture containing an enzyme and a drug and/or its metabolite(s) and is favorable in eliminating removal of the enzyme.

As the packing material to be coated, a wide range of materials can be used including those commonly used in chromatography such as silica gel, polystyrene, polymethylmethacrylate, glass and modified glass, as well as substances which can usually be shaped, e.g., any high molecular compounds other than the above, ceramics, etc.

The temperature-responsive polymer may be coated over the packing material in any manner, for example, according to the procedures described in JP 2-211865 A. Namely, the coating may be accomplished, e.g., by attaching the above polymer to the packing material via a coupling agent or the like, or by coating the above monomer or polymer through any one of electron beam irradiation (EB), γ-irradiation, ultraviolet irradiation, plasma treatment, corona treatment or organic polymerization, or through physical adsorption such as application or kneading.

To illustrate the foregoing, an example will be given below using poly(N-isopropylacrylamide) as a temperature-responsive polymer. Poly(N-isopropylacrylamide) is known as a polymer having a lower critical solution temperature of 31° C. and, when in free form, will be dehydrated in water at a temperature above 31° C. to cause aggregation of polymer chains and hence cloudiness. In contrast, at a temperature below 31° C., polymer chains will be hydrated and dissolved in water. In the present invention, this polymer is coated and immobilized on the surface of the packing material. Thus, upon reaching a temperature above 31° C., the polymer on the substrate surface will also be dehydrated and will impart hydrophobic properties to the surface because polymer chains are coated and immobilized on the substrate surface. In contrast, at a temperature below 31° C., the polymer on the substrate surface will be hydrated and will impart hydrophilic properties to the substrate surface because polymer chains are coated and immobilized on the substrate surface.

The evaluation system for drug-metabolizing capacity thus obtained provides an extremely effective technique in a clinical setting as a simple method for evaluating the drug-metabolizing capacity in patients. This system is also expected to be effective as an evaluation means for P450 genetic polymorphism when used for direct measurement of cytochrome P450 functions. Moreover, this system also enables the diagnosis of cirrhosis and liver cancer when used for confirmation of P450 functions.

EXAMPLES

The present invention will now be further illustrated by way of the following examples, which are not intended to limit the scope of the invention.

Example 1

(a) Synthesis Procedures for Poly(N-Isopropylacrylamide) Having a Carboxyl Group at One End N-Isopropylacrylamide (20.0 g), 3-mercaptopropionic acid (0.09 g) and 2,2'-azobis(isobutyronitrile) (0.21 g) were introduced into a polymerization tube and dissolved by addition of dry N,N-dimethylformamide (50 ml). After freezing under liquid nitrogen, oxygen in the polymerization tube was degassed by a vacuum oil pump and the polymerization tube kept under reduced pressure was soaked in methanol to remove dissolved oxygen in N,N-dimethylformamide. This freezing/degassing operation was repeated three times. After completion of the degassing, the tube was reacted for 20 hours in an incubator at 70±1° C. After cooling to room temperature, the reaction mixture was concentrated under reduced pressure. And then the raction mixture wasadded dropwise to dry diethyl ether to precipitate poly(N-isopropylacrylamide) having a carboxyl group at one end. This precipitate was collected by filtration through a PTFE (polytetrafluoroethylene) filter (pore size: 3.0 µm) and dried under reduced pressure in a desiccator containing silica gel to give a crude product (19.0 g). This crude product was dissolved in dry N,N'-dimethylformamide (30 ml) and then added dropwise to dry diethyl ether, followed by filtration through a teflon filter to collect the resulting precipitate. This precipitate was dried under reduced pressure in a desiccator to give purified poly(N-isopropylacrylamide). The resulting polymer was analyzed by gel filtration chromatography using tetrahydrofuran as a solvent and by acid-base measurement, confirming that poly(N-isopropylacrylamide) had a molecular weight of 15,000 and had about one carboxyl group at its molecular end.

(b) Active Esterification of Poly(N-Isopropylacrylamide) Having a Carboxyl Group at One End The purified poly(N-isopropylacrylamide) (11.35 g) was dissolved in dry ethyl acetate (100 ml), followed by addition of dicyclohexylcarbodiimide (1.23 g) and N-hydroxysuccinimide (0.69 g). While stirring well, the mixture was reacted at 0° C. for 2 hours and then at room temperature (20° C. to 25° C.) for 12 hours. After the reaction mixture was filtered through a PTFE filter to remove a by-product N,N'-dicyclohexylurea, the resulting filtrate was concentrated under reduced pressure and then added dropwise to dry diethyl ether. The precipitate was collected by filtration through a teflon filter and evaporated at normal temperature under reduced pressure to remove the solvent, thereby obtaining esterified poly(N-isopropylacrylamide).

(c) Coupling Between Esterified Poly(N-Isopropylacrylamide) and Amino Group Carrier The esterified poly(N-isopropylacrylamide) (2.0 g) was dissolved in pure water (50 ml), followed by addition of aminopropyl silica gel (6.0 g). After being reacted by vigorous shaking for 12 hours at room temperature, the reaction mixture was washed with cold water (500 ml), added again to a solution of an additional esterified poly(N-isopropylacrylamide) (2.0 g) in pure water (50 ml) and then vigorously shaken for 12 hours at room temperature. This operation was repeated three times. The reaction mixture was washed sequentially with cold water (500 ml) and methanol (100 ml) and then dried. The esterified poly(N-isopropylacrylamide) (3.0 g) was dissolved in N,N-dimethylformamide (6 ml). This solution was added in 1 ml aliquots at 30 minute intervals and mixed by gentle inversion with a solution prepared by dilution with pure water (24 ml) from a suspension (1 ml) of polystyrene microparticles whose surface was modified with primary amino groups (diameter: 1.0±0.03 µm, stock concentration: $5 \times 10^{11}$ particles/ml). After adding the whole volume of the esterified poly(N-isopropylacrylamide) solution, the reaction mixture was mixed by inversion at 4° C. or below for 16 hours. After completion of the reaction, collection by centrifugation and washing by cold purification were repeated twice, followed by dilution with Hanks' balanced salt solution (pH 7.4) ($6 \times 10^9$, $6 \times 10^{10}$/ml)

Reagents Used

Testosterone (biochemical grade, Wako Pure Chemical Industries, Ltd., Japan)

Potassium dihydrogen phosphate (Wako Pure Chemical Industries, Ltd., Japan)

Disodium hydrogen phosphate (Wako Pure Chemical Industries, Ltd., Japan)

NADPH Regenerating System Solution A (NADPH A) (BD GENTEST)

NADPH Regenerating System Solution B (NADPH B) (BD GENTEST)

Human CYP3A4+reductase, microsomal (BD GENTEST)

HPLC-grade methanol (Wako Pure Chemical Industries, Ltd., Japan)

HPLC-grade acetonitrile (Wako Pure Chemical Industries, Ltd., Japan)

Solid phase extraction Sep-pak® Plus C18 (Waters)

Apparatuses Used

Analytical high performance liquid chromatography

Pump (L-7100, HITACHI)

UV detector (L-7405, HITACHI)

Integrator (D-7000, HITACHI)

Column oven (AO-30C, Shodex)

Packing material (poly-(N-isopropylacrylamide)-immobilized packing material)

Experimental Procedures

Testosterone was metabolized in vitro and the poly-(N-isopropylacrylamide)-modified packing material was used to separate testosterone and 6β-hydroxytestosterone with water alone.

The in vitro metabolism was performed in accordance with the following procedure. NADPH Regenerating System Solutions A and B containing P450 (CYP3A4, 20 pmol), $NADP^+$ (1.3 mM), glucose-6-phosphate (3.3 mM), $MgCl_2$ (3.3 mM), glucose-6-phosphate dehydrogenase (0.4 U/mL) and testosterone (0.2 mM) were added and dissolved in 100 mM phosphate buffer (pH 7.4) to give a total volume of 0.5 mL (CYP3A4: 10 μL, NADPH A: 25 μL, NADPH B: 5 μL, phosphate buffer: 445 μL, testosterone: 1 mg/mL, methanol: 5 μL). After incubation for 10 minutes at 37° C., the reaction was stopped by addition of acetonitrile (250 μL). After centrifugation for 3 minutes, the resulting supernatant was evaporated, dissolved in purified water (1 mL), extracted using solid phase extraction on Sep-pak® Plus C18 and then eluted with methanol/purified water (60:40). This solution was evaporated and dissolved in purified water (1 mL) for use as a sample.

Results

First, a commonly used ODS column was used to analyze a mixture of commercially available testosterone and its metabolite 6β-hydroxytestosterone (reference standard). The eluent used was purified water containing as much as 60% methanol (purified water/methanol=40:60). The results indicated that both substances could be separated at retention times of 3.91 min for 6β-hydroxytestosterone and 11.45 min for testosterone.

Next, a P-(NIPAAm) column was used for analysis. The results obtained are shown in FIG. 1. Separation was performed under conditions using water alone to examine differences in retention between high and low temperatures. At 10° C., 6β-hydroxytestosterone and testosterone were observed to be successfully separated although they both had retention times within 10 minutes (3.01 min for 6β-hydroxytestosterone and 6.88 min for testosterone). When similarly analyzed at 40° C., both 6β-hydroxytestosterone and testosterone had extended retention times of 5.16 min and 18.11 min, respectively. This result indicated that the retention time could be adjusted by changing the column temperature even using purified water alone as an eluent, which was a feature of this column.

Next, the same analysis was performed on the sample metabolized in vitro. The sample receiving only metabolism could not be analyzed at 10° C. because the sample was contaminated with contaminants originating from the enzymes or the NADPH Regenerating System Solutions. For this reason, the sample was subjected to solid phase extraction on Sep-pak®, indicating that the contaminants could be washed away to leave only target peaks behind. The sample thus treated was analyzed at 10° C. and 40° C. At 10° C., 6β-hydroxytestosterone could not be successfully separated due to interference from peaks of the remaining enzymes which were not fully washed away. In the expectation that the retention time of 6β-hydroxytestosterone would be delayed as in the case of the results obtained for the reference standard, the analysis was performed at 40° C. and succeeded in achieving successful separation of 6β-hydroxytestosterone at a retention time of 7.21 min. It was also observed that the retention time of testosterone was extended from 7.21 min to 18.11 min.

These results are shown in FIG. 1. The measurement conditions were shown below, along with the retention times of the reference standard and the metabolized sample at 10° C. and 40° C.

<Measurement Conditions>

UV=254 nm

Water (mobile phase) flow rate=1.0 mL/min

Sample volume injected=20 μL

TABLE 1

| | Retention time (min) | |
|---|---|---|
| <Reference standard> | 10° C. | 40° C. |
| 6β-Hydroxytestosterone | 3.01 | 5.16 |
| Testosterone | 6.88 | 18.11 |

TABLE 2

| | Retention time (min) | |
|---|---|---|
| <Metabolized sample> | 10° C. | 40° C. |
| 6β-Hydroxytestosterone | 3.04 | 5.16 |
| Testosterone | 7.21 | 18.21 |

Example 2

Each of caffeine, warfarin and omeprazole reagents was dissolved in water or THF to give a saturated aqueous solution. Each solution was filtered through a 0.45 μm filter and the resulting filtrate was used as a sample.

Apparatuses Used

Analytical high performance liquid chromatography

Pump (L-7100, HITACHI)

Mobile phase flow rate 1.0 mL/min

Integrator (D-7000, HITACHI)

Column oven (AO-30C, Shodex)

Packing material (poly-(N-isopropylacrylamide)-immobilized packing material)

Results

Each of the caffeine, warfarin and omeprazole samples was separated by analytical high performance liquid chromatography and the retention time was measured for each sample at 10° C. and 50° C. with UV wavelength indicated below.

Caffeine (mobile phase: water) (UV=275 nm)

S-Warfarin (mobile phase: water) (UV=302 nm)

Omeprazole (mobile phase: water) (UV=302 nm)

The results obtained are shown in Table 3.

TABLE 3

Table Retention times at 10° C. and 50° C.

| | Retention time (min) | |
|---|---|---|
| | 10° C. | 50° C. |
| Caffeine | 2.57 | 2.36 |
| S-Warfarin | 15.71 | 6.91 |
| Omeprazole | 9.52 | 4.84 |

The above results indicate that this technique allows separation of these CYP probe drugs using water alone.

This column is environmentally friendly because it achieves separation using an eluent composed of water alone. Moreover, since today there is a strong demand for tailormade medical technology, pharmacists in a clinical setting will use HPLC for confirmation of CYP phenotypes in the near future. It is therefore believed that a system will be required, which uses water alone as an eluent and which allows separation simply by temperature control.

Example 3

Figure 2:
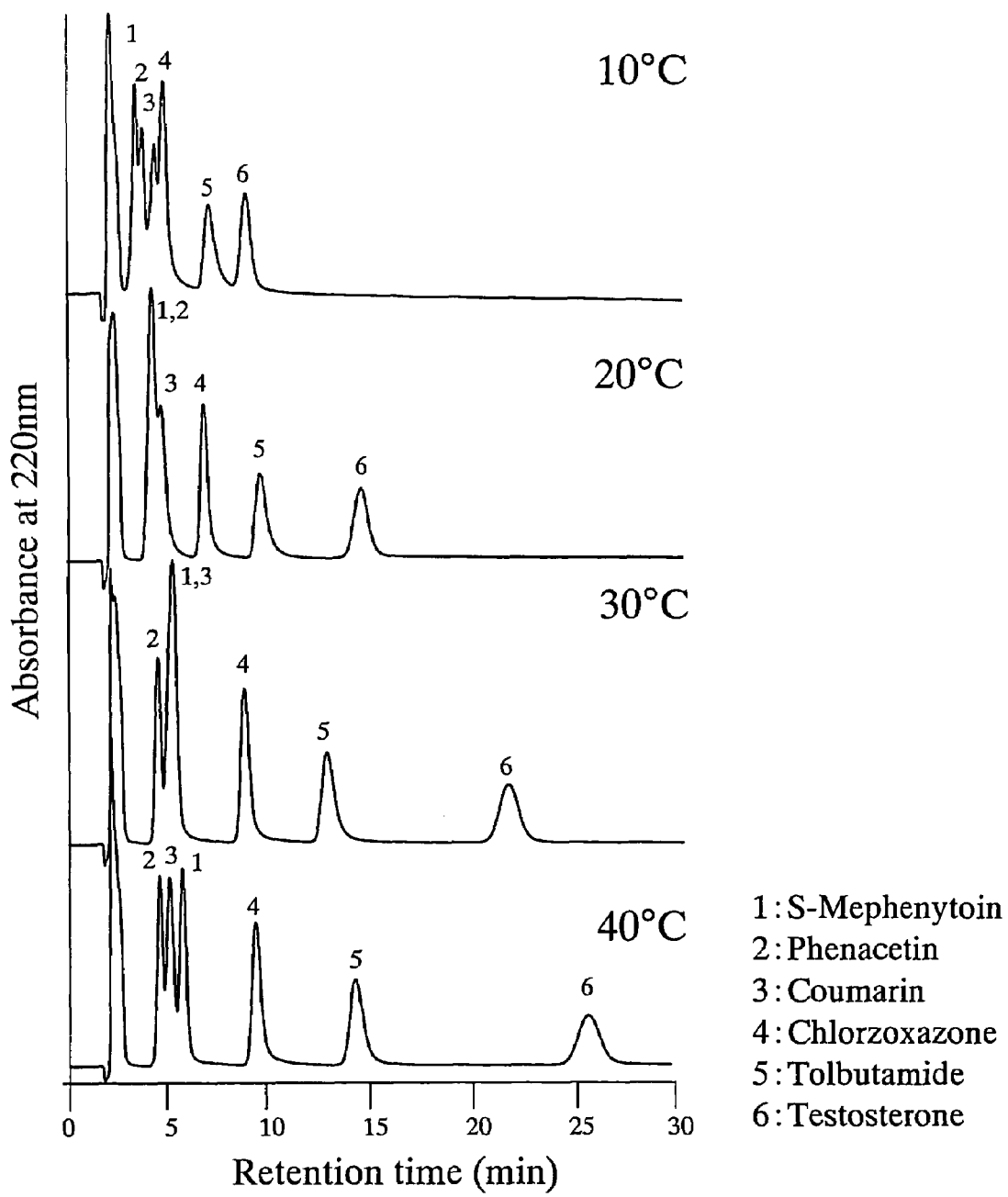
FIG. 2 presents charts showing the results of the simultaneous analysis performed on a mixed sample of 6 probe drugs using analytical high performance liquid chromatography at various temperatures.

The poly-(N-isopropylacrylamide)-immobilized packing material shown in Example 1 was used to simultaneously analyze a mixed sample of 6 probe drugs. Phenacetin (1A2), tolbutamide (2C9), S-mephenyloin (2C19), testosterone (3A4), coumarin (2A6) and chlorzoxazone (2E1) were prepared at the concentrations indicated in Table 4 using THF as a solvent. The structural formulae of these probe drugs are shown in Table 5. The results obtained are shown in FIG. 2. As can be seen from FIG. 2, it is indicated that using the poly-(N-isopropylacrylamide)-immobilized packing material of the present invention enables the separation of useful probe drugs and that individual signals are more successfully separated at a higher separation temperature.

TABLE 4

| | Probe drug | | | | | |
|---|---|---|---|---|---|---|
| | Phenacetin | Tolbutamide | S-Mephenytoin | Testosterone | Chlorzoxazone | Coumarin |
| Concentration (mg/mL) | 0.25 | 0.25 | 0.25 | 0.5 | 0.25 | 0.25 |
| Mixing ratio | 1 | 1 | 3 | 1 | 1.5 | 1.5 |

TABLE 5

Structures of CYP probe drugs

| | Structural formula | M.W. | logP |
|---|---|---|---|
| Phenacetin (CYP1A2) | | 179.22 | 0.985 |
| (S)-Mephenytoin (CYP2C19) | | 218.26 | 1.540 |
| Coumarin (CYP2A6) | | 146.15 | 1.820 |
| Chrorzoxazone (CYP2E1) | | 169.57 | 2.238 |
| Tolbutamide (CYP2C9) | | 270.35 | 2.473 |
| Testosterone (CYP3A4) | | 288.43 | 2.899 |

Example 4

Urine and serum pre-treated with Sep-Pak® Plus C18 Cartridges were used as biological samples and spiked with the same 6 probe drugs as used in Example 3. The samples thus prepared were analyzed.

Pre-treatment of the biological samples was performed as follows.

Urine sample: Urine was collected in a harn cup, 5 mL of which was taken and subjected to solid phase extraction. The solid phase extraction was accomplished by passing the urine through a filter warmed up with methanol/Milli-Q water, washing away hydrophilic substances with Milli-Q water and then collecting target substances with methanol. The collected methanol fraction was evaporated to completely remove the solvent and then dissolved again in 5 mL THF for use as a blank sample.

Serum sample: A lyophilized serum pool for quality control (Nissui) was taken in a volume of 5 mL and subjected to solid phase extraction. The solid phase extraction was accomplished by passing the serum through a filter warmed up with methanol/Milli-Q water/0.1 M $CH_3COONH_4$ (pH=4.8), washing away hydrophilic substances with 0.1 M $CH_3COONH_4$ (pH=4.8) and then collecting target substances with methanol. The collected methanol fraction was evaporated to completely remove the solvent and then dissolved again in 5 mL THF for use as a blank sample.

<Experimental Conditions>

Pump: L-7100 (HITACHI)

UV detector: L-7400 (HITACHI)

Integrator: D-7500 (HITACHI)

Column Oven: AO-30C (Shodex)

For temperature stabilization, a 1 m metal loop was used as a pre-heat tube.

Eluent: 0.1 M $CH_3COONH_4$ (pH=4.8)

Flow rate: 1.0 mL/min

Detection wavelength: UV=220 nm

Temperature: 10, 20, 30, 40° C.

Column: poly-(N-isopropylacrylamide)-immobilized packing material

<Results>

Figure 3:
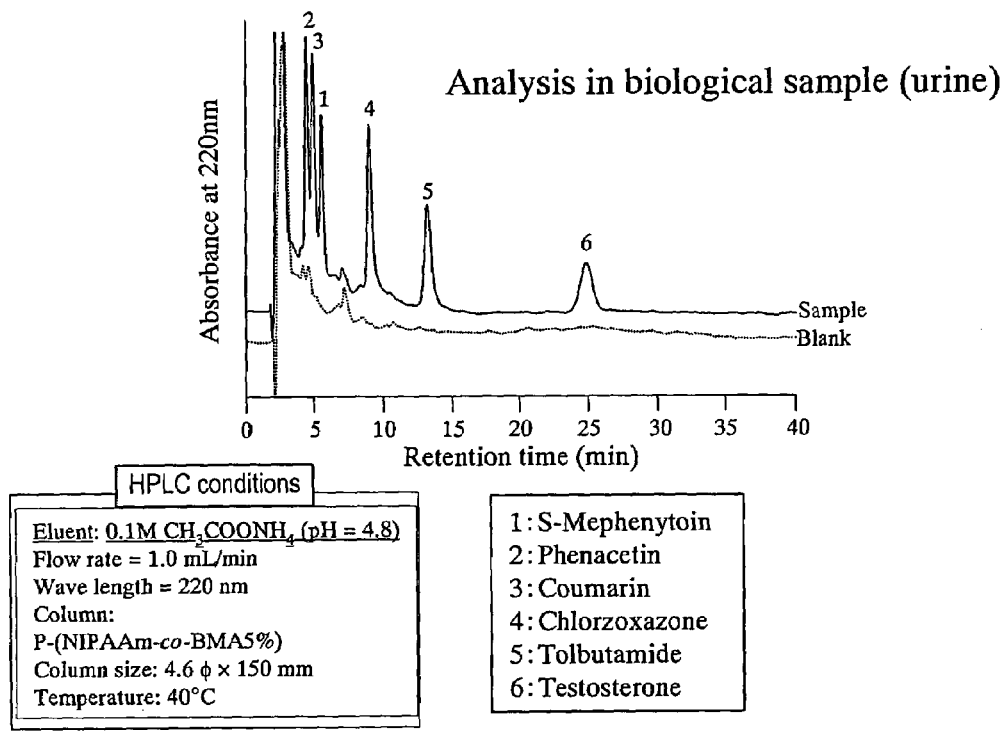
FIG. 3 presents charts showing the results of the analysis in which urine and serum pre-treated with Sep-Pak® Plus C18 Cartridges were used as biological samples and spiked with the 6 probe drugs shown in Example 3.
Figure 3:
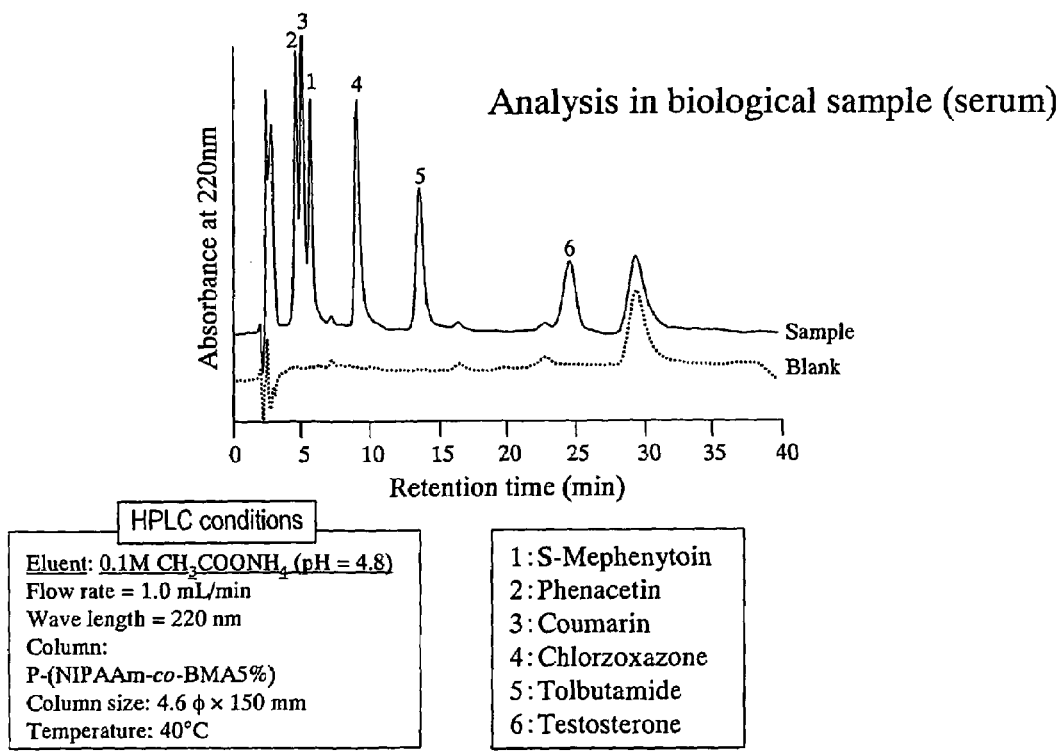

The results obtained are shown in FIG. 3. As can be seen from the figure, it is indicated that the probes listed in Example 3 can be separated even in the form of a mixture containing a biological sample.

Example 5

CYP1A2 is an enzyme catalyzing N-demethylation on the N3 nitrogen atom of caffeine, O-deethylation of phenacetin to acetaminophen, etc. Since N-demethylation of caffeine constitutes 80% to 90% of the total caffeine metabolism in humans and relies on CYP1A2 activity, caffeine is used as an in vivo probe drug for this enzyme. However, caffeine is used less often in vitro because, due to the detection limit of HPLC, caffeine is required to be labeled with a radioactive substance or analyzed using LC/MS.

<Samples>

Phenacetin and acetaminophen were each dissolved at a concentration of 0.2 mg/mL in an eluent (0.1 M ammonium acetate, pH=4.8) for use as samples. Moreover, a 1:1 mixed solution was prepared and used as a sample.

<Measurement>

UV=220 nm,

Poly-(N-isopropylacrylamide)-immobilized packing material,

Temperature: 5, 10, 20, 30, 40° C.

Eluent: 0.1 M $CH_3COONH_4$ (pH=4.8)

For temperature stabilization, a 1 m metal loop was used as a pre-heat tube.

<Results>

Figure 4:
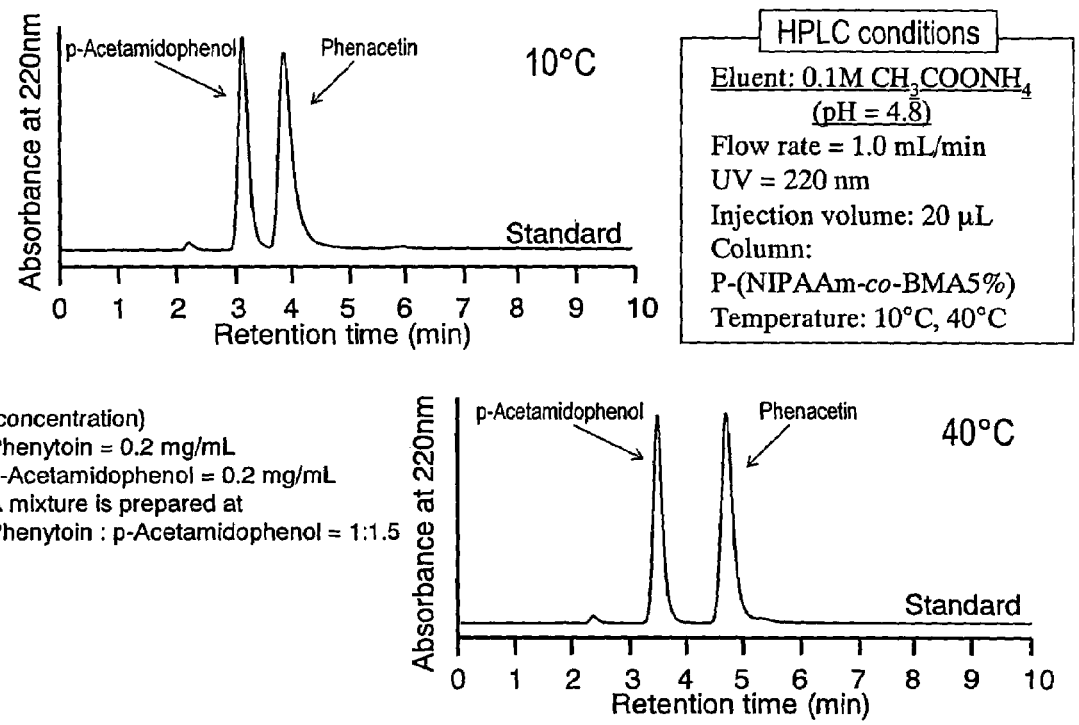
FIG. 4 presents charts showing the results of the analysis performed on a 1:1 mixed sample of phenacetin and acetaminophen.

The results obtained are shown in FIG. 4 and Table 6. Analysis at 10° C. confirmed that peaks of phenacetin and acetaminophen were separated at both 10° C. and 40° C. These peaks also had good shapes and were eluted in order of log P values from low to high. The results indicate that a probe drug and its metabolite can be analyzed simultaneously.

TABLE 6

| Temperature (° C.) | Acetaminophen Retention time (min) | Phenacetin Retention time (min) |
|---|---|---|
| 5 | 3.12 | 3.82 |
| 10 | 3.16 | 3.87 |
| 20 | 3.32 | 4.13 |
| 30 | 3.46 | 4.49 |
| 40 | 3.46 | 4.65 |

Example 6

S-Mephenyloin and 4-hydroxymephenyloin (reference standard) were analyzed simultaneously. The CYP2C9 enzyme catalyzes N-demethylation of diazepam, N-demethylation of imipramine, 5-hydroxylation of omeprazole, etc. No structural feature has been identified for drugs serving as substrates. S-Mephenyloin is frequently used for in vitro metabolism experiments.

<Samples>

S-Mephenyloin and 4'-hydroxymephenyloin were each dissolved at their saturation concentration in an eluent (0.1 M ammonium acetate, pH=4.8) for use as samples. The saturated solutions were mixed at a ratio of S-mephenyloin to 4'-hydroxymephenyloin of 1.5:1.

<Results>

Figure 5:
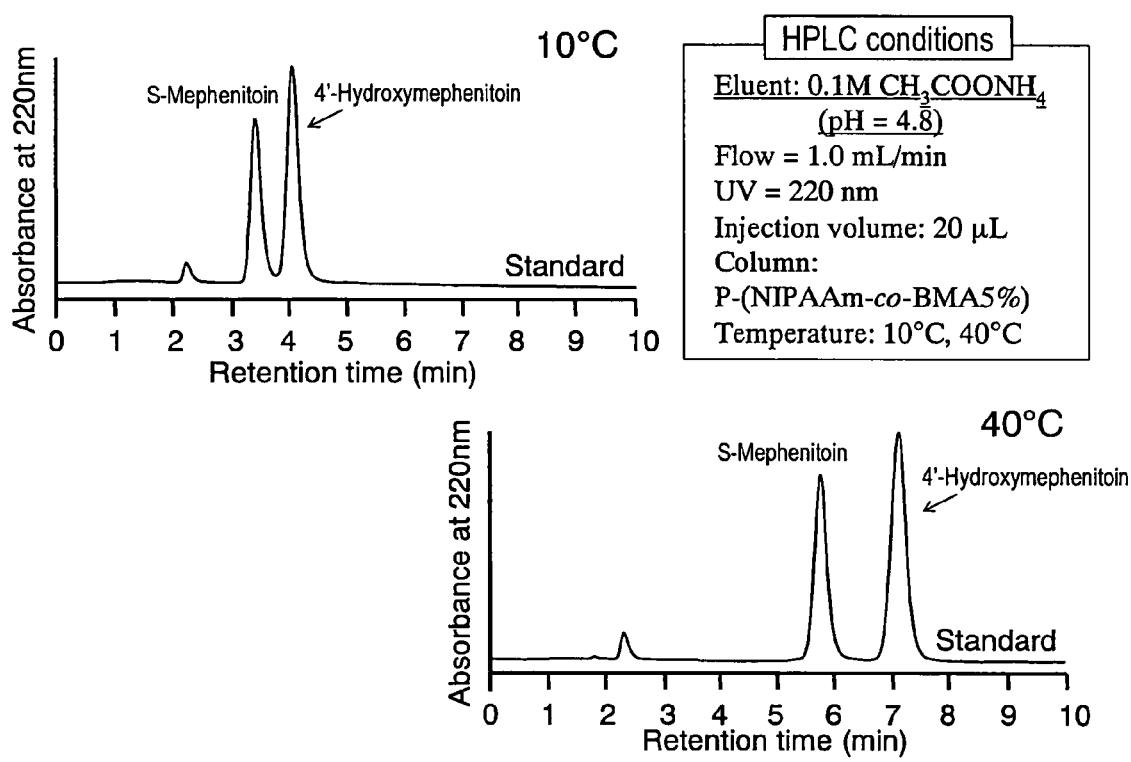
FIG. 5 presents charts showing the results of the analysis performed on a 1.5:1 mixed sample of S-mephenyloin and 4'-hydroxymephenyloin.

The results obtained are shown in FIG. 5 and Table 7. The peak positions of the substrate and its metabolite were in the opposite order to that expected. Interactions other than hydrophobic interaction may also contribute to this result. However, the analysis per se achieved successful separation by increasing the temperature. Temperature-induced variations in retention time were observed to be increased when compared to phenacetin and acetaminophen. The results indicate that a probe drug and its metabolite can be analyzed simultaneously.

TABLE 7

| Temperature (° C.) | 4'-Hydroxymephenytoin Retention time (min) | S-Mephenytoin Retention time (min) |
|---|---|---|
| 5 | 3.72 | 3.21 |
| 10 | 4.04 | 3.41 |
| 20 | 5.32 | 4.19 |
| 30 | 6.73 | 5.23 |
| 40 | 7.12 | 5.77 |

Example 7

Without being pre-treated with Sep-Pak® Plus C18 Cartridges, the same biological urine and serum samples as used in Example 4 were spiked with the following 3 probe drugs: chlorzoxazone (2E1 enzyme probe drug), tolbutamide (2C9 enzyme probe drug) and testosterone (3A4 enzyme probe drug). The samples thus prepared were analyzed.

<Experimental Conditions>

Pump: L-7100 (HITACHI)

UV detector: L-7400 (HITACHI)

Integrator: D-7500 (HITACHI)

Column Oven: AO-30C (Shodex)

For temperature stabilization, a 1 m metal loop was used as a pre-heat tube.

Eluent: 0.1 M $CH_3COONH_4$ (pH=4.8)

Flow rate: 1.0 mL/min

Detection wavelength: UV=220 nm

Temperature: 10, 20, 30, 40° C.

Column: poly-(N-isopropylacrylamide)-immobilized packing material

<Results>

When measured at 40° C., peaks of chlorzoxazone (2E1 enzyme probe drug), tolbutamide (2C9 enzyme probe drug) and testosterone (3A4 enzyme probe drug) could be observed. The results indicated that biological components and probe drugs could be separated from each other even in the form of a mixture containing a biological sample.

INDUSTRIAL APPLICABILITY

The present invention enables proper evaluation of drug-metabolizing capacity through simple means without adversely affecting the environment.

The invention claimed is:

1. A method for measurement of an amount of drug metabolized by a specific drug metabolizing enzyme and/or an amount of the resulting metabolite(s), the method comprising:
   (a) preparing a sample to be measured, wherein the sample to be measured comprises the drug and/or its metabolite (s):
   (b) separating solutes in the sample by high performance liquid chromatography with an aqueous mobile phase under temperature control using a packing material whose surface is coated with a temperature responsive polymer having a hydration force varying in the temperature range of 0° C. to 80° C.; and
   (c) measuring the amount of drug metabolized by a specific drug metabolizing enzyme and/or the amount of the resulting metabolite(s).

2. The method according to claim 1, wherein the sample to be measured is a mixture of (i) a specific drug metabolizing enzyme and (ii) a drug and/or its metabolite(s).

3. The method according to claim 1, wherein the drug metabolizing enzyme comprises one or more members selected from the group consisting of cytochrome P450 molecular species, alcohol dehydrogenase, esterase and β-glucuronidase.

4. The method according to claim 3, wherein one or more members selected from the group consisting of CYP1A1, CYP1A2, CYP2A6, CYP2B6, CYP2C8, CYP2CQ CYP2C19, CYP2DR CYP2E1, CYP2F1 CYP3A3, CYP3A4 and CYP3A7 are measured simultaneously as the cytochrome P450 molecular species.

5. The method according to claim 1, wherein the temperature responsive polymer having a hydration force varying in the temperature range of 0° C. to 80° C. has a lower critical solution temperature when in free form.

6. The method according to claim 5, wherein the temperature responsive polymer has a crosslinked structure.

7. The method according to claim 5, wherein the temperature responsive polymer is polyalkylacrylamide and/or a copolymerization product thereof.

8. The method according to claim 7, wherein the polyalkylacrylamide is poly-(N-isopropylacrylamide) and/or poly-(N, N-diethylacrylamide).

9. An evaluation method for drug metabolizing capacity, the method comprising:
   (a) measuring the amount of drug metabolized by a specific drug metabolizing enzyme and/or the amount of the resulting metabolite(s) according to claim 1 and
   (b) evaluating drug metabolizing capacity in a patient who provides the sample from such measurement(s).

10. An evaluation method for cytochrome P450 genetic polymorphism, the method comprising:
    (a) measuring the amount of drug metabolized by a specific drug metabolizing enzyme and/or the amount of the resulting metabolite(s) according to claim 1 and
    (b) evaluating cytochrome P450 genetic polymorphism in a patient who provides the sample from such measurement(s).

11. The method according to claim 2, wherein the drug metabolizing enzyme comprises one or more members selected from the group consisting of cytochrome P450 molecular species, alcohol dehydrogenase, esterase and β-glucuronidase.

12. The method according to claim 11, wherein one or more members selected from the group consisting of CYP1A1, CYP1A2, CYP2A6, CYP2B6, CYP2C8, CYP2C9, CYP2C19, CYP2D6, CYP2E1, CYP2F1, CYP3A3, CYP3A4 and CYP3A7 are measured simultaneously as the cytochrome P450 molecular species.

13. The method according to claim 1, wherein the temperature responsive polymer having a hydration force varying in the temperature range of 0° to 80° has an upper critical solution temperature when in free form.

14. The method according to claim 13, wherein the temperature responsive polymer has a crosslinked structure.

15. The method according to claim 6, wherein the temperature responsive polymer is polyalkylacrylamide and/or a copolymerization product thereof.

* * * * *